(12) United States Patent
Ci

(10) Patent No.: US 10,485,842 B2
(45) Date of Patent: Nov. 26, 2019

(54) CHINESE HERBAL ORAL PASTE FOR CONDITIONING YANG DEFICIENCY CONSTITUTION AND PROCESSING METHOD THEREOF

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 0 days.

(21) Appl. No.: 15/967,027

(22) Filed: Apr. 30, 2018

(65) Prior Publication Data

US 2019/0192608 A1    Jun. 27, 2019

(30) Foreign Application Priority Data

Dec. 26, 2017 (CN) .......................... 2017 1 1428987

(51) Int. Cl.

| | |
|---|---|
| *A61K 36/00* | (2006.01) |
| *A61K 36/8945* | (2006.01) |
| *A61K 36/64* | (2006.01) |
| *A61K 36/39* | (2006.01) |
| *A61K 36/232* | (2006.01) |
| *A61K 36/46* | (2006.01) |
| *A61K 36/815* | (2006.01) |
| *A61K 36/54* | (2006.01) |
| *A61K 36/71* | (2006.01) |
| *A61K 36/258* | (2006.01) |
| *A61K 35/50* | (2015.01) |
| *A61K 47/26* | (2006.01) |
| *A61K 45/06* | (2006.01) |
| *A61K 9/00* | (2006.01) |
| *A61K 36/40* | (2006.01) |
| *A61K 9/06* | (2006.01) |

(52) U.S. Cl.
CPC ........ *A61K 36/8945* (2013.01); *A61K 9/0053* (2013.01); *A61K 9/0056* (2013.01); *A61K 9/06* (2013.01); *A61K 35/50* (2013.01); *A61K 36/232* (2013.01); *A61K 36/258* (2013.01); *A61K 36/39* (2013.01); *A61K 36/40* (2013.01); *A61K 36/46* (2013.01); *A61K 36/54* (2013.01); *A61K 36/64* (2013.01); *A61K 36/71* (2013.01); *A61K 36/815* (2013.01); *A61K 45/06* (2013.01); *A61K 47/26* (2013.01); *A61K 2236/13* (2013.01); *A61K 2236/51* (2013.01)

(58) Field of Classification Search
None
See application file for complete search history.

*Primary Examiner* — Qiuwen Mi
(74) *Attorney, Agent, or Firm* — Novick, Kim & Lee, PLLC; Allen Xue

(57) ABSTRACT

The present application discloses a Chinese herbal oral paste for conditioning yang deficiency constitution. The Chinese herbal oral paste includes the following raw material components: prepared rehmannia root, Chinese yam, dogberry, seed of Chinese dodder, angelica, eucommia ulmoides, lycium barbarum, cinnamon, fuling, cortex moutan, rhizoma alismatis, white atractylodes rhizome, radix polygonum multiflorum preparata, dried ginseng, processed aconite root, pprepared liquorice root, cumin, herba cistanche, fruit of Chinese magnoliavine, radix cyathulae, raspberry, nutmeg, fructus broussonetiae, epimedium, fructus psoraleae, rhizoma curculiginis, rhizoma acori graminei, morinda officinalis, human placenta, cynomorium songaricum, bitter cardamon, semen allii tuberosi, antler gelatin, xylitol, walnut kernel, and donkey-hide gelatin. The Chinese herbal oral paste of the present disclosure has a higher drug concentration and good taste, is particularly suitable for health preserving in winter and conditioning the yang deficiency constitution and is capable of achieving certain efficacy of strengthening physical health.

20 Claims, 1 Drawing Sheet

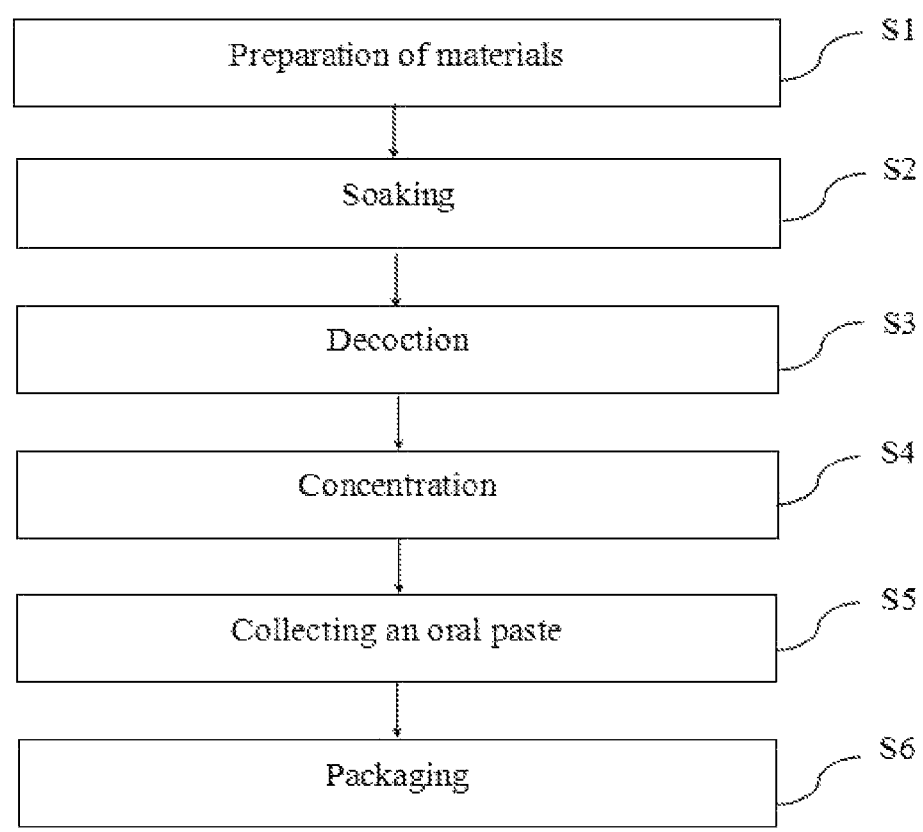

CHINESE HERBAL ORAL PASTE FOR CONDITIONING YANG DEFICIENCY CONSTITUTION AND PROCESSING METHOD THEREOF

TECHNICAL FIELD

The present disclosure relates to the field of health foods, and particularly to a Chinese herbal oral paste for conditioning yang deficiency constitution and a processing method thereof.

BACKGROUND

In *Classification and Determination of Constitution in Traditional Chinese Medicine*, the China Association of Chinese Medicine classifies body constitutions of the human body into nine types, i.e., yin-yang harmony constitution, yang deficiency constitution, qi deficiency constitution, phlegm-dampness constitution, damp-heat constitution, qi depression constitution, blood stasis constitution, and allergic constitution, most of which are sub-healthy states.

The yang deficiency constitution manifests insufficiency of yang qi (vital energy) in the body and interior cold due to yang deficiency when the internal organs (zang and fu) of the human body dysfunction, usually showing pale facial complexion, weak breath, physical tiredness and somnolence, aversion to cold and chilly limbs, general weakness or limb edema, pale and fat tongue with indentation, slightly white tongue fur, deep pulse and inertia, and is mostly caused by insufficient inborn endowment, in addition to outside pathogenic cold and eating too much cold food, extreme anxieties, intemperance in sexual life, and long illness. The tendency of morbidity is: being susceptible to diseases such as phlegm and retained fluid, swelling, and diarrhea, being resistant to summer but nonresistant to winter, and being susceptible to wind, cold, and dampness pathogen.

Such sub-healthy constitution as yang deficiency constitution belongs to chronic diseases and has a relatively long disease course, and requires a long-term medication and gradual conditioning, in order to achieve the effects of tonifying qi and nourishing qi. The dosage forms commonly used in the traditional Chinese medicine are decoctions and Chinese patent medicine such as pills and the like. Decoctions usually have relatively good efficacy, but the administration thereof is complicated, and the taste thereof is poor, if the decoctions need to be administered for a long time, it is difficult for a patient to keep taking the decoctions. Moreover, the efficacy of the pills is relatively poor.

It is mentioned in the *Inner Canon of the Yellow Emperor* that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and determines the susceptibility to diseases. It is believed in the traditional Chinese medicine that since the human beings live in the natural world, physiological functions of the human body usually change with seasons, that is, "correspondence between man and nature". Winter is the season when the human body "stores energies", and appropriate nourishment can enhance the constitution, ward off diseases and strengthen the body, and prolong life, that is, conditioning in winter or nourishing in winter commonly mentioned in the traditional Chinese medicine. For the sub-healthy population with yang deficiency constitution, to choose a solid oral paste with a higher drug concentration and good taste, and being convenient to carry is more adapted to requirements of modern people for conditioning in winter or nourishing in winter.

SUMMARY

A main object of the present disclosure is to provide a Chinese herbal nourishing product suitable for conditioning in winter so as to condition yang deficiency constitution.

In order to achieve the above object, according to one aspect of the present disclosure, there is provided a Chinese herbal oral paste for conditioning yang deficiency constitution.

The Chinese herbal oral paste for conditioning yang deficiency constitution according to the present disclosure includes the following raw material components in parts by weight: 4-20 parts of prepared rehmannia root, 10-20 parts of Chinese yam, 10-20 parts of dogberry, 5-15 parts of seed of Chinese dodder, 5-15 parts of angelica, 5-15 parts of eucommia ulmoides, 9-21 parts of lycium barbarum, 3-9 parts of cinnamon, 8-22 parts of fuling, 3-9 parts of cortex moutan, 3-9 parts of rhizoma alismatis, 6-18 parts of white atractylodes rhizome, 10-30 parts of radix polygonum multiflorum preparata, 4-8 parts of dried ginseng, 5-15 parts of processed aconite root, 4-8 parts of pprepared liquorice root, 3-9 parts of cumin, 7-17 parts of herba cistanche, 3-9 parts of fruit of Chinese magnoliavine, 5-15 parts of radix cyathulae, 5-15 parts of raspberry, 1-5 parts of nutmeg, 5-15 parts of fructus broussonetiae, 7-23 parts of epimedium, 5-15 parts of fructus psoraleae, 8-22 parts of rhizoma curculiginis, 3-9 parts of rhizoma acori graminei, 7-17 parts of morinda officinalis, 1-5 parts of human placenta, 7-23 parts of cynomorium songaricum, 7-23 parts of bitter cardamon, 5-15 parts of semen allii tuberosi, 10-30 parts of antler gelatin, 15-35 parts of xylitol, 20-40 parts of walnut kernel, and 20-40 parts of donkey-hide gelatin.

Furthermore, the Chinese herbal oral paste for conditioning yang deficiency constitution according to the present disclosure includes the following raw material components in parts by weight: 8-16 parts by weight of prepared rehmannia root, 12-18 parts by weight of Chinese yam, 12-18 parts by weight of dogberry, 8-12 parts by weight of seed of Chinese dodder, 8-12 parts by weight of angelica, 8-12 parts by weight of eucommia ulmoides, 12-18 parts by weight of lycium barbarum, 5-7 parts by weight of cinnamon, 12-18 parts by weight of fuling, 5-7 parts by weight of cortex moutan, 5-7 parts by weight of rhizoma alismatis, 9-15 parts by weight of white atractylodes rhizome, 15-25 parts by weight of radix polygonum multiflorum preparata, 5-7 parts by weight of dried ginseng, 8-12 parts by weight of processed aconite root, 5-7 parts by weight of pprepared liquorice root, 5-7 parts by weight of cumin, 10-14 parts by weight of herba cistanche, 5-7 parts by weight of fruit of Chinese magnoliavine, 8-12 parts by weight of radix cyathulae, 8-12 parts by weight of raspberry, 2-4 parts by weight of nutmeg, 8-12 parts by weight of fructus broussonetiae, 11-19 parts by weight of epimedium, 8-12 parts by weight of fructus psoraleae, 11-19 parts by weight of rhizoma curculiginis, 5-7 parts by weight of rhizoma acori graminei, 10-14 parts by weight of morinda officinalis, 2-4 parts by weight of human placenta, 11-19 parts by weight of cynomorium songaricum, 11-19 parts by weight of bitter cardamon, 8-12 parts by weight of semen allii tuberosi, 16-24 parts by weight of antler gelatin, 20-30 parts by weight of xylitol, 25-35 parts by weight of walnut kernel, and 25-35 parts by weight of donkey-hide gelatin.

Furthermore, the Chinese herbal oral paste for conditioning yang deficiency constitution according to the present disclosure includes the following raw material components in parts by weight: 12 parts by weight of prepared rehmannia root, 15 parts by weight of Chinese yam, 15 parts by weight of dogberry, 10 parts by weight of seed of Chinese dodder, 10 parts by weight of angelica, 10 parts by weight of eucommia ulmoides, 15 parts by weight of lycium barbarum, 6 parts by weight of cinnamon, 15 parts by weight of fuling, 6 parts by weight of cortex moutan, 6 parts by weight of rhizoma alismatis, 12 parts by weight of white atractylodes rhizome, 20 parts by weight of radix polygonum multiflorum preparata, 6 parts by weight of dried ginseng, 10 parts by weight of processed aconite root, 6 parts by weight of pprepared liquorice root, 6 parts by weight of cumin, 12 parts by weight of herba cistanche, 6 parts by weight of fruit of Chinese magnoliavine, 10 parts by weight of radix cyathulae, 10 parts by weight of raspberry, 3 parts by weight of nutmeg, 10 parts by weight of fructus broussonetiae, 15 parts by weight of epimedium, 10 parts by weight of fructus psoraleae, 15 parts by weight of rhizoma curculiginis, 6 parts by weight of rhizoma acori graminei, 12 parts by weight of morinda officinalis, 3 parts by weight of human placenta, 15 parts by weight of cynomorium songaricum, 15 parts by weight of bitter cardamon, 10 parts by weight of semen allii tuberosi, 20 parts by weight of antler gelatin, 25 parts by weight of xylitol, 30 parts by weight of walnut kernel, and 30 parts by weight of donkey-hide gelatin.

In order to achieve the above object, according to the other aspect of the present disclosure, there is provided a processing method for a Chinese herbal oral paste for conditioning yang deficiency constitution.

The processing method for a Chinese herbal oral paste for conditioning yang deficiency constitution according to the present disclosure includes the following steps in sequence: preparation of materials, soaking, decoction, concentration, and collecting an oral paste.

Furthermore, the step of preparation of materials is: measuring raw materials of formula amounts according to composition of the Chinese herbal oral paste, and cleaning raw materials, except antler gelatin, donkey-hide gelatin, and xylitol, for subsequent use.

Furthermore, the soaking step is: soaking the cleaned raw materials with 8-10 folds of water for 8-15 h, with the water over the raw materials by 10-20 cm.

Furthermore, the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining decoction juice with the squeezed juice, followed by static settlement for 2 h, and filtering, to obtain a supernatant liquid for subsequent use.

Furthermore, the concentration step is: boiling and skimming the supernatant liquid resulted in the decoction step, followed by decoction concentration and stirring with gentle heat, until the drug liquid does not disperse when being dropped on paper, to obtain a vegetarian paste.

Furthermore, the step of collecting an oral paste is: pouring xylitol, and melted antler gelatin and donkey-hide gelatin into the vegetarian paste respectively, cooking them slowly with low heat, stirring them continuously with a shovel, until the juice coagulates into beads when dropped into clear water and does not disperse, and canning the resulted oral paste.

The melting step is: smashing lumps of antler gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

The Chinese herbal oral paste of the present disclosure has a higher drug concentration and good taste, is particularly suitable for health preserving in winter and conditioning the yang deficiency constitution, will not create negative effects or harm to the human body at all, and is capable of achieving certain efficacy of strengthening physical health.

BRIEF DESCRIPTION OF DRAWINGS

The accompanying drawing, which constitutes a part of the present application, is used to provide a further understanding of the present disclosure, so that other features, objects, and advantages of the present application become more obvious. The illustrative drawings for embodiments of the present disclosure and the description thereof are used to explain the present disclosure, rather than constitute an improper limitation on the present disclosure. In the drawing, FIG. 1 is a flow chart of a processing technology for a Chinese herbal oral paste of an embodiment of the present disclosure.

DETAILED DESCRIPTION OF EMBODIMENTS

In order to enable a person skilled in the art to better understand the solutions of the present application, the technical solutions of the embodiments of the present disclosure will be described clearly and completely below with reference to the accompanying drawing of the embodiments of the present application. Apparently, the embodiments described are merely for some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below in combination with the embodiments.

A Chinese herbal oral paste for conditioning yang deficiency constitution according to the present disclosure includes the following raw material components: prepared rehmannia root, Chinese yam, dogberry, seed of Chinese dodder, angelica, eucommia ulmoides, lycium barbarum, cinnamon, fuling, cortex moutan, rhizoma alismatis, white atractylodes rhizome, radix polygonum multiflorum preparata, dried ginseng, processed aconite root, pprepared liquorice root, cumin, herba cistanche, fruit of Chinese magnoliavine, radix cyathulae, raspberry, nutmeg, fructus broussonetiae, epimedium, fructus psoraleae, rhizoma curculiginis, rhizoma acori graminei, morinda officinalis, human placenta, cynomorium songaricum, bitter cardamon, semen allii tuberosi, antler gelatin, xylitol, walnut kernel, donkey-hide gelatin.

Prepared rehmannia root is sweet in flavor and warm in nature, acts on liver and kidney, nourishes blood and moistens dryness, replenishes essence and supplements marrow, and is used for blood-deficiency etiolation, vertigo and palpitation, irregular menstruation, flooding, liver-kidney yin depletion, tidal fever and night sweating, gonobolia and impotence, infertility, irregular menstruation, metrorrhagia embolism in blood, soreness and weakness of waist and knees, tinnitus and hearing loss, dizziness, premature graying of hair, consumptive thirst, constipation, and kidney-deficiency panting.

Chinese yam is sweet in flavor, neutral in nature, and non-toxic, acts on spleen, lung, and kidney, strengthens spleen and stomach, nourishes lung qi, tonifies kidney essence, nourishes physical health, renders good hearing and eyesight and delays senility upon long administration, and is used for reduced spleen-deficiency appetite, loose stool diarrhea, lung-deficiency asthma, gonobolia and frequent urination, and yin-deficiency consumptive thirst.

Dogberry is sour and astringent in flavor and slightly warm in nature, acts on liver and kidney, nourishes liver and kidney, induces astringency and relieves desertion, and is used for vertigo and tinnitus, soreness and weakness of waist and knees, impotence and gonobolia, enuresis and frequent urination, metrorrhagia and leucorrhoea, hyperhidrosis prostration, and internal-heat consumptive thirst.

Seed of Chinese dodder is acrid and sweet in flavor and neutral in nature, acts on liver, kidney, and spleen, nourishes liver and kidney, secures essence and reduces urination, prevents miscarriage, improves eyesight, cures diarrhea, eliminates wind and removes freckles upon external application, and is used for kidney-deficiency backache, impotence and gonobolia, frequent urination, blurred vision, spleen-deficiency diarrhea, and threatened abortion.

Angelica is sweet and acrid in flavor and warm in nature, acts on liver, heart, and spleen, replenishes blood and invigorates the circulation of blood, regulates menstruation and relieves pain, relaxes bowel, and is used for blood-deficiency etiolation, vertigo and palpitation, irregular menstruation, amenorrhea and dysmenorrhea, deficiency-cold stomachache, rheumatic arthralgia, traumatic injury, ulcer and skin and external diseases, and constipation due to intestinal dryness.

Eucommia ulmoides is sweet in flavor and warm in nature, acts on liver and kidney, nourishes liver and kidney, treats aches in spinal column, impotent feet and knees, dribble of urine, vulval wet itching, and hypertension, and has the efficacy of preventing miscarriage.

Lycium barbarum is sweet in flavor and neutral in nature, acts on liver and kidney, has the efficacies of nourishing kidney and essence, and nourishing liver to improve eyesight, and is used for liver and kidney yin deficiency, soreness and weakness of waist and knees, dizziness, visual deterioration, consumptive thirst, and spermatorrhea.

Cinnamon is acrid and sweet in flavor and extremely hot in nature, acts on kidney, spleen, heart, and liver, tonifies fire and helps yang, guides fire to origin, eliminates cold to stop pain, warms meridians, and is used for impotence and uterine cold, waist and knee crymodynia, kidney-deficiency asthma, yang deficiency with upper manifestation, vertigo and hot eyes, heart and abdomen crymodynia, deficiency-cold vomiting and diarrhea, cold abdominal colic stomachache, and dysmenorrhea and amenorrhea Fuling is sweet and light in flavor and neutral in nature, acts on heart, lung, spleen, and kidney, clears dampness and promotes diuresis, tonifies spleen, calms mind, and is used for edema and scanty urine, phlegm and fluid retention and palpitation, reduced spleen-deficiency appetite, loose stool and diarrhea, uneasiness, and palpitation and insomnia.

Cortex moutan is bitter and acrid in flavor and slightly cold in nature, acts on heart, liver, and stomach, removes heat to cool blood, removes blood stasis, eliminates steaming heat, and is used for blood-heat haematemesis, eruption, yin-deficiency internal heat, sweatless steaming bone, amenorrhea and algomenorrhea, traumatic injury, swelling pain of skin and external diseases, and intestinal carbuncle and stomachache.

Rhizoma alismatis is sweet in flavor and cold in nature, acts on kidney and bladder, alleviates water retention, promotes diuresis, reduces heat, and is used for difficult urination, edema distention, vomiting, diarrhea, phlegm-fluid retention, dermatophytosis, gonorrhea, and hematuria.

White atractylodes rhizome is bitter and sweet in flavor and warm in nature, acts on spleen and stomach, tonifies spleen and qi, dries dampness and clears dampness from urination, constrains sweating, prevents miscarriage, and is used for reduced spleen-deficiency appetite, abdominal distension diarrhea, phlegm and fluid retention and palpitation, edema, spontaneous perspiration, and fetal upset.

Radix polygonum multiflorum preparata is bitter, sweet, and astringent in flavor and slightly warm in nature, acts on liver, heart, and kidney, nourishes liver and kidney, tonifies essence and blood, blackens hair and beard, strengthens muscles and bones, resolves turbidity and lowers lipid, and is used for blood-deficiency etiolation, vertigo and tinnitus, premature graying of hair, soreness and weakness of waist and knees, numbness of limb, metrorrhagia and leucorrhoea, and hyperlipemia.

Dried ginseng is sweet and slightly bitter in taste and warm in nature, acts on spleen and lung, replenishes qi and relieves desertion, nourishes lung and spleen, promotes the secretion of body fluid, calms mind, develops intelligence, and is used for prostration after serious diseases, long illness, or hemorrhea, lung-deficiency short breath and panting, reduced spleen-deficiency appetite, tiredness, regurgitation, chronic diarrhea, kidney-deficiency impotence, frequent urination, rectocele, body fluid impairment and thirst after illness, hyperhidrosis, palpitation, insomnia and amnesia, metrorrhagia and metrostaxis, and infantile chronic fright.

Processed aconite root is acrid and sweet in flavor and toxic, and extremely hot in nature, acts on heart, kidney, and spleen, restores yang, tonifies fire and helps yang, eliminates cold to stop pain, and is used for yang depletion, cold extremities and pulse weakness, impotence and uterus cold, abdominal cold and pain, yin-cold edema, and wind-cold-dampness arthralgia.

Prepared liquorice root is sweet in flavor and neutral in nature, acts on heart, lung, spleen, and stomach, nourishes spleen and stomach, supplements qi and restores pulse, and is used for spleen and stomach weakness, tiredness, palpitation, and irregular pulse.

Cumin is acrid in flavor and warm in nature, acts on liver, kidney, spleen, and stomach, eliminates cold to stop pain, regulates circulation of qi and harmonizes stomach, and is used for cold abdominal colic and abdominal pain, testicle sagging, dysmenorrhea, lower abdomen pain, abdominal distention, and reduced appetite and vomiting.

Herba cistanche is sweet and salty in flavor and warm in nature, acts on kidney and large intestines, nourishes kidney yang, replenishes essence and blood, moistens intestines, and is used for kidney-yang deficiency and senility, impotence due to insufficient essence and blood, spermatorrhea, gonorrhea, frequent urination and dribble of urine, backache and leg weakness, tinnitus and blurred vision, irregular menstruation, uterus cold and infertility, and constipation due to intestinal dryness.

Fruit of chinese magnoliavine is sour in flavor and warm in nature, acts on lung, kidney, and heart, astringes lung, nourishes kidney, promotes the secretion of body fluid, constrains sweating, arrests seminal emission, and is used for kidney-deficiency asthma, mouth dryness and thirst, spontaneous perspiration, night sweating, internal lesion caused by overexertion and emaciation, wet dream and spermatorrhea, and chronic diarrhea and dysentery.

Radix cyathulae is sweet and slightly bitter in flavor and neutral in nature, acts on liver and kidney, eliminates stasis and restores menstrual flow, eases joint movement, induces inducing diuresis for treating stranguria, and is used for amenorrhea and abdominal mass, retention of placenta, traumatic injury, rheumatic arthralgia, motor impairment of feet, hematuria and stranguria due to hematuria and other diseases.

Raspberry is sweet and sour in flavor and warm in nature, acts on liver, kidney, and urinary bladder, invigorates kidney to secure essence and reduce urination, and nourishes the liver to improve eyesight, and is used for gonobolia and spermatorrhea, enuresis and frequent urination, impotence and premature ejaculation, and blurred and dim vision.

Nutmeg is acrid in flavor and warm in nature, acts on spleen, stomach, and large intestines, warms the middle energizer and astringes intestine, promotes the circulation of qi and helps digestion, and is used for deficiency diarrhea, cold dysentery, abdominal distention, reduced appetite and vomiting, and indigestion.

Fructus broussonetiae is sweet in flavor and cold in nature, acts on liver, spleen, and kidney, tonifies kidney and clears liver, improves eyesight, promotes urination, and is used for soreness and weakness of waist and knees, consumptive steaming bone, dizziness, cataract, and edema and distention.

Epimedium is acrid and sweet in flavor and warm in nature, acts on liver and kidney, invigorates kidney and strengthens yang, dispels wind and dampness, and is used for kidney-deficiency impotence, waist and knees weakness, wind-cold-dampness arthralgia, and ache in muscles and bones.

Fructus psoraleae is bitter and acrid in flavor and warm in nature, acts on kidney and spleen, invigorates kidney and strengthens yang, secures essence and reduces urination, treats kidney-deficiency backache, frequent urination, infantile enuresis, and kidney deficiency, warms spleen and cures diarrhea, absorbs qi and relieves asthma, and is used to treat kidney-deficiency impotence, soreness, weakness and crymodynia of waist and knees, kidney-deficiency gonobolia, enuresis, frequent urination, morning diarrhea due to yang deficiency of spleen and kidney, deficiency-cold asthma due to the kidney's inability to absorb qi and so on.

Rhizoma curculiginis is acrid in flavor, toxic, and hot in nature, acts on kidney, warms kidney and invigorates yang, eliminates cold and dampness, and is used for impotence and cold sperm, urinary incontinence, abdominal fullness crymodynia, soreness and ache of waist and knees, weak sinews and bones, muscular constriction of lower limbs, and climacteric syndrome.

Rhizoma acori graminei is acrid and bitter in flavor and warm in nature, acts on heart and stomach, resolves dampness and stimulates appetite, induces resuscitation and eliminates phlegm, refreshes spirit and develops intelligence, regulates circulation of qi, invigorates circulation of blood, relieves heat, eliminates dampness, and is used for fullness and distending pain in the chest and upper abdomen and anorexia, anorectic dysentery, unconsciousness and epilepsy, amnesia and hearing loss, epilepsy, coma due to blocking of the respiratory system, pyreticosis and unconsciousness, amnesia, deafness with stagnation, depression in heart and chest, stomachache, bellyache, wind-cold-dampness arthralgia, ulcer and pyogenic infection, and traumatic injury.

Morinda officinalis is sweet and acrid in flavor and slightly warm in nature, acts on kidney and liver, replenishes kidney yang, strengthens bones and muscles, dispels winddampness, and is used for impotence and gonobolia, uterus cold and infertility, irregular menstruation, lower abdomen pain, rheumatic arthralgia, and motor impairment of muscles and bones.

Human placenta is sweet and salty in flavor and warm in nature, acts on lung, heart, and kidney, nourishes kidney and essence, reinforces qi and nourishes blood, and is used for asthenic diseases, emaciation, hemoptysis and asthma, consumptive heat and steaming bone, gonobolia and other diseases.

Cynomorium songaricum is sweet in flavor and warm in nature, acts on liver, kidney, and large intestines, nourishes kidney yang, replenishes essence and blood, moistens intestines, and is used for kidney-yang insufficiency, essence and blood insufficiency, motor impairment of waist and knees, impotence and spermatorrhea, and constipation due to intestinal dryness.

Bitter cardamon is acrid in flavor and warm in nature, acts on spleen and kidney, warms spleen, cures diarrhea, and assimilates saliva, warms kidney, reduces urination, and arrests spontaneous emission, and is used for spleen and stomach deficiency and coldness, vomiting, diarrhea, cold pain in the abdomen, excessive saliva in mouth, kidney-deficiency enuresis, frequent urination, gonobolia, and gonorrhea.

Semen allii tuberosi is acrid and sweet in flavor and warm in nature, acts on liver and kidney, nourishes liver and kidney, tonifies yang and arrests spontaneous emission, and is used for kidney-deficiency impotence, soreness and weakness of waist and knees, gonobolia, frequent urination, turbid urine, and thin morbid leucorrhea.

Antler gelatin is sweet and salty in flavor and warm in nature, acts on kidney and liver, warms and nourishes liver and kidney, replenishes essence and nourishes blood, and is used for blood deficiency dizziness, soreness and coldness in waist and knees, and consumptive emaciation.

Ealnut kernel is sweet in flavor and warm in nature, acts on kidney, lung, and large intestines, tonifies kidney and strengthens waist, warms lung and relieves asthma, relaxes bowel, and is used for backache and leg weakness, chronic deficiency dyspnea, and constipation due to intestinal dryness.

Donkey-hide gelatin is sweet in flavor and neutral in nature, acts on lung, liver, and kidney, replenishes blood and nourishes yin, moistens dryness, stops bleeding, and is used for blood-deficiency etiolation, vertigo and palpitation, dysphoria insomnia, and lung dryness cough.

The yang deficiency constitution is mostly caused by dysfunctions of internal organs such as insufficient inborn endowment, outside pathogenic cold, eating too much cold food, extreme anxieties, prolonged illness, and intemperance in sexual life, "with yang waning and yin waxing", generating interior cold due to excess cold yin-qi, showing insufficiency of yang-qi, reduced functions of the body such as warming, promoting, evaporation, and gasification, even the syndrome of water retention. Conditioning the yang deficiency constitution is based on the principle of warming yang and strengthening health. In view of yang deficiency of the human body, the Chinese herbal oral paste of the present application additionally adds drugs nourishing yin while mainly using drugs tonifying yang, so as to finally achieve the object of nourishing yang by nourishing yin. The yang-qi deficiency of the yang deficiency constitution can be supplemented by combining various drugs. With the multiple types of drug materials of large dosages, efficacies of the various drug materials generate a synergistic effect, with the functions of warming yang and tonifying kidney, and can be used for conditioning the yang deficiency constitution, so that people are vigorous with strong resistibility, and avoid the occurrence of diseases. With the conditioning for such constitution, it is more targeted and will not create side effects, without harm to the human body at all, and can achieve certain efficacy of strengthening the body.

As shown in FIG. 1, the processing method for the Chinese herbal oral paste for conditioning yang deficiency constitution of the present disclosure includes the following steps in sequence: preparation of materials, soaking, decoction, concentration, collecting an oral paste, and finally packaging. For specific operations of respective steps, reference can be made to various embodiments of the present disclosure.

Embodiment 1:

A Chinese herbal oral paste for conditioning yang deficiency constitution includes the following raw material components in parts by weight: 4 parts of prepared rehmannia root, 10 parts of Chinese yam, 10 parts of dogberry, 5 parts of seed of Chinese dodder, 5 parts of angelica, 5 parts of eucommia ulmoides, 9 parts of lycium barbarum, 3 parts of cinnamon, 8 parts of fuling, 3 parts of cortex moutan, 3 parts of rhizoma alismatis, 6 parts of white atractylodes rhizome, 10 parts of radix polygonum multiflorum preparata, 4 parts of dried ginseng, 5 parts of processed aconite root, 4 parts of pprepared liquorice root, 3 parts of cumin, 7 parts of herba cistanche, 3 parts of fruit of Chinese magnoliavine, 5 parts of radix cyathulae, 5 parts of raspberry, 1 parts of nutmeg, 5 parts of fructus broussonetiae, 7 parts of epimedium, 5 parts of fructus psoraleae, 8 parts of rhizoma curculiginis, 3 parts of rhizoma acori graminei, 7 parts of morinda officinalis, 1 parts of human placenta, 7 parts of cynomorium songaricum, 7 parts of bitter cardamon, 5 parts of semen allii tuberosi, 10 parts of antler gelatin, 15 parts of xylitol, 20 parts of walnut kernel, and 20 parts of donkey-hide gelatin.

The processing method thereof includes the following steps in sequence: preparation of materials: measuring raw materials of formula amounts according to composition of the Chinese herbal oral paste, and cleaning raw materials, except antler gelatin, donkey-hide gelatin, and xylitol, for subsequent use;

soaking: soaking the cleaned raw materials with 8 folds of water for 8 h, with the water over the raw materials by 10 cm;

decoction: decocting the soaked drug materials over flame, firstly boiling the drug materials with high heat to sufficiently expand, then boiling the drug materials with low heat for 1 hour of decoction, then filtering the drug juice with gauze, then soaking filtered dregs of decoction with clear water and decocting the soaked dregs of decoction with low heat for 1 hour, repeated 4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted antler gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of antler gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 2:

A Chinese herbal oral paste for conditioning yang deficiency constitution includes the following raw material components in parts by weight: 20 parts of prepared rehmannia root, 20 parts of Chinese yam, 20 parts of dogberry, 15 parts of seed of Chinese dodder, 15 parts of angelica, 15 parts of eucommia ulmoides, 21 parts of lycium barbarum, 9 parts of cinnamon, 22 parts of fuling, 9 parts of cortex moutan, 9 parts of rhizoma alismatis, 18 parts of white atractylodes rhizome, 30 parts of radix polygonum multiflorum preparata, 8 parts of dried ginseng, 15 parts of processed aconite root, 8 parts of pprepared liquorice root, 9 parts of cumin, 17 parts of herba cistanche, 9 parts of fruit of Chinese magnoliavine, 15 parts of radix cyathulae, 15 parts of raspberry, 5 parts of nutmeg, 15 parts of fructus broussonetiae, 23 parts of epimedium, 15 parts of fructus psoraleae, 22 parts of rhizoma curculiginis, 9 parts of rhizoma acori graminei, 17 parts of morinda officinalis, 5 parts of human placenta, 23 parts of cynomorium songaricum, 23 parts of bitter cardamon, 15 parts of semen allii tuberosi, 30 parts of antler gelatin, 35 parts of xylitol, 40 parts of walnut kernel, and 40 parts of donkey-hide gelatin.

The processing method therefor includes the following steps in sequence:

preparation of materials: measuring raw materials of formula amounts according to composition of the Chinese herbal oral paste, and cleaning raw materials, except antler gelatin, donkey-hide gelatin, and xylitol, for subsequent use;

soaking: soaking the cleaned raw materials with 10 folds of water for 15 h, with the water over the raw materials by 20 cm;

decoction: decocting the soaked drug materials over flame, firstly boiling the drug materials with high heat to sufficiently expand, then boiling the drug materials with low heat for 2 hours of decoction, then filtering the drug juice with gauze, then soaking filtered dregs of decoction with clear water and decocting the soaked dregs of decoction with low heat for 1 hour, repeated 2 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted antler gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of antler gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 3:

A Chinese herbal oral paste for conditioning yang deficiency constitution includes the following components in parts by weight: 8 parts of prepared rehmannia root, 12 parts of Chinese yam, 12 parts of dogberry, 8 parts of seed of Chinese dodder, 8 parts of angelica, 8 parts of eucommia ulmoides, 12 parts of lycium barbarum, 5 parts of cinnamon, 12 parts of fuling, 5 parts of cortex moutan, 5 parts of rhizoma alismatis, 9 parts of white atractylodes rhizome, 15 parts of radix polygonum multiflorum preparata, 5 parts of dried ginseng, 8 parts of processed aconite root, 5 parts of pprepared liquorice root, 5 parts of cumin, 10 parts of herba cistanche, 5 parts of fruit of Chinese magnoliavine, 8 parts of radix cyathulae, 8 parts of raspberry, 2 parts of nutmeg, 8 parts of fructus broussonetiae, 11 parts of epimedium, 8 parts of fructus psoraleae, 11 parts of rhizoma curculiginis, 5 parts of rhizoma acori graminei, 10 parts of morinda officinalis, 2 parts of human placenta, 11 parts of cynomorium songaricum, 11 parts of bitter cardamon, 8 parts of semen allii tuberosi, 16 parts of antler gelatin, 20 parts of xylitol, 25 parts of walnut kernel, and 25 parts of donkey-hide gelatin.

The processing method thereof includes the following steps in sequence:

preparation of materials: measuring raw materials of formula amounts according to composition of the Chinese herbal oral paste, and cleaning raw materials, except antler gelatin, donkey-hide gelatin, and xylitol, for subsequent use;

soaking: soaking the cleaned raw materials with 9 folds of water for 10 h, with the water over the raw materials by 12 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted antler gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of antler gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 4:

A Chinese herbal oral paste for conditioning yang deficiency constitution includes the following components in parts by weight: 16 parts of prepared rehmannia root, 18 parts of Chinese yam, 18 parts of dogberry, 12 parts of seed of Chinese dodder, 12 parts of angelica, 12 parts of eucommia ulmoides, 18 parts of lycium barbarum, 7 parts of cinnamon, 18 parts of fuling, 7 parts of cortex moutan, 7 parts of rhizoma alismatis, 15 parts of white atractylodes rhizome, 25 parts of radix polygonum multiflorum preparata, 7 parts of dried ginseng, 12 parts of processed aconite root, 7 parts of pprepared liquorice root, 7 parts of cumin, 14 parts of herba cistanche, 7 parts of fruit of Chinese magnoliavine, 12 parts of radix cyathulae, 12 parts of raspberry, 4 parts of nutmeg, 12 parts of fructus broussonetiae, 19 parts of epimedium, 12 parts of fructus psoraleae, 19 parts of rhizoma curculiginis, 7 parts of rhizoma acori graminei, 14 parts of morinda officinalis, 4 parts of human placenta, 19 parts of cynomorium songaricum, 19 parts of bitter cardamon, 12 parts of semen allii tuberosi, 24 parts of antler gelatin, 30 parts of xylitol, 35 parts of walnut kernel, and 35 parts of donkey-hide gelatin.

The processing method therefor includes the following steps in sequence:

preparation of materials: measuring raw materials of formula amounts according to composition of the Chinese herbal oral paste, and cleaning raw materials, except antler gelatin, donkey-hide gelatin, and xylitol, for subsequent use;

soaking: soaking the cleaned raw materials with 9 folds of water for 11 h, with the water over the raw materials by 14 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted antler gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of antler gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

Embodiment 5:

A Chinese herbal oral paste for conditioning yang deficiency constitution includes the following components in parts by weight: 12 parts of prepared rehmannia root, 15 parts of Chinese yam, 15 parts of dogberry, 10 parts of seed of Chinese dodder, 10 parts of angelica, 10 parts of eucommia ulmoides, 15 parts of lycium barbarum, 6 parts of cinnamon, 15 parts of fuling, 6 parts of cortex moutan, 6 parts of rhizoma alismatis, 12 parts of white atractylodes rhizome, 20 parts of radix polygonum multiflorum preparata, 6 parts of dried ginseng, 10 parts of processed aconite root, 6 parts of pprepared liquorice root, 6 parts of cumin, 12 parts of herba cistanche, 6 parts of fruit of Chinese magnoliavine, 10 parts of radix cyathulae, 10 parts of raspberry, 3 parts of nutmeg, 10 parts of fructus broussonetiae, 15 parts of epimedium, 10 parts of fructus psoraleae, 15 parts of rhizoma curculiginis, 6 parts of rhizoma acori graminei, 12 parts of morinda officinalis, 3 parts of human placenta, 15 parts of cynomorium songaricum, 15 parts of bitter cardamon, 10 parts of semen allii tuberosi, 20 parts of antler gelatin, 25 parts of xylitol, 30 parts of walnut kernel, and 30 parts of donkey-hide gelatin.

The processing method therefor includes the following steps in sequence:

preparation of materials: measuring raw materials of formula amounts according to composition of the Chinese herbal oral paste, and cleaning raw materials, except antler gelatin, donkey-hide gelatin, and xylitol, for subsequent use;

soaking: soaking the cleaned raw materials with 9 folds of water for 13 h, with the water over the raw materials by 15 cm;

decoction: decocting the soaked drug materials over flame, firstly boiling the drug materials with high heat to sufficiently expand, then boiling the drug materials with low heat for 1.5 hours of decoction, then filtering the drug juice with gauze, then soaking filtered dregs of decoction with clear water and decocting the soaked dregs of decoction with low heat for 1 hour, repeated 3 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by decoction concentration and stirring with gentle heat, until a drug liquid does not disperse when being dropped on paper, to obtain a vegetarian paste;

collecting an oral paste: pouring xylitol, and melted antler gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

In the above, the step of melting gelatin type drugs is: smashing lumps of antler gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

EXPERIMENT EXAMPLE 1

Below is a test of effects of the Chinese herbal oral paste for conditioning yang deficiency constitution prepared according to Embodiment 5 of the present disclosure.

Basic conditions of cases: 100 clinical cases of yang deficiency constitution, including 50 male cases and 50 female cases. 40 cases were aged and suffered from long term of illness, soreness and cold of waist and knees, lassitude, aversion to cold, impotence, spermatorrhea, loose stool, and frequent clear urination; 30 cases suffered from oral ulcer, spontaneous perspiration, aversion to cold and chilly limbs, physical lassitude, slightly white tongue coating, and deep pulse and inertia; 30 cases suffered from soreness of waist and leg weakness, physical aversion to cold, spasm in lower abdomen, difficult or frequent urination, pale and fat tongue, deep and thin pulse, phlegm and asthma, oedema, dermatophytosis, consumptive thirst, and chromatic diarrhea.

Usage and dosage: 25 g each time, once a day. Brew 25 g of the oral paste with boiling water in a cup, and stirring it to melt for administration.

Evaluation criteria for therapeutic effects:

Cured: clinical symptoms were completely eliminated, and normal life was restored.

Effective: clinical symptoms were partially eliminated, and various signs were gradually improved.

Ineffective: symptoms and signs were not obviously improved.

Result statistics: 51 cases cured, effective to 35 cases, and ineffective to 14 cases, i.e., effective to 86 cases in total, therefore the total effective rate was 86%.

EXPERIMENT EXAMPLE 2

Influence on Models of Yang-deficiency Mice

Experiment method: 70 kunming mice, half males and half females, with a body weight of 200±15 kg, equally divided into 7 groups, namely, (1) a normal control group; (2) a yang-deficiency model group (hydrocortisone 25.0 mg/kg+NS); (3) groups of Embodiments 1-5 (hydrocortisone 25.0 mg/kg+0.4 g/kg of the Chinese herbal oral paste prepared according to Embodiments 1-5). The groups of Embodiments 1-5 were subcutaneously injected with hydrocortisone while being fed with the particles of the Chinese herbal oral paste by gavage. The hydrocortisone was injected subcutaneously for 8 d, and the gavage was continued for 10 d, and then the following indexes were observed on the 10th day: (1) spontaneous activities: after each mouse was adapted for 5 min, recording times of activities of the mice in every 10 min; (2) low-temperature swimming time: putting the mice in water at a water temperature of 6-8° C., and observing the swimming time of the mice, where it indicated swimming disability when a mouse sunk down for 6 s but could not come out. The experiment results are shown in Table 1

TABLE 1

Influence of Particles of the Chinese Herbal Oral Paste of the Present disclosure on Models of Yang-deficiency Mice

| Group | Low-temperature Swimming Time (min) | Spontaneous Activities (times/10 min) |
| --- | --- | --- |
| Normal Control Group | 5.76 ± 1.03 | 760 ± 111 |
| Yang-deficiency Model Group | 4.38 ± 1.27 | 430 ± 144 |
| Embodiment 1 | 5.59 ± 1.18 | 742 ± 128 |
| Embodiment 2 | 5.78 ± 1.06 | 773 ± 135 |
| Embodiment 3 | 5.56 ± 1.22 | 699 ± 124 |

TABLE 1-continued

Influence of Particles of the Chinese Herbal Oral Paste of the Present disclosure on Models of Yang-deficiency Mice

| Group | Low-temperature Swimming Time (min) | Spontaneous Activities (times/10 min) |
|---|---|---|
| Embodiment 4 | 5.92 ± 1.19 | 731 ± 98 |
| Embodiment 5 | 5.66 ± 1.42 | 767 ± 107 |

It can be seen from data in the above table that the low-temperature swimming time and the spontaneous activities of the yang-deficiency mice are significantly increased in Embodiments 1-5 of the present disclosure, of which the effects are obviously superior to the yang-deficiency model group. The Chinese herbal oral paste provided in the present disclosure has certain effects of conditioning the yang deficiency constitution.

It should be indicated that Embodiments 1-5 of the present invention are merely some of the embodiments for implementing the technical solutions of the present invention, and should not be construed as the scope of protection of the present invention merely limited to the above five embodiments, and a person skilled in the art can make further improvements on the basis of the present invention without departing from the principle and spirit of the present invention.

For example, the components of the Chinese herbal oral paste of the present invention are not limited to those listed in respective embodiments, while other Chinese herbal medicines also can be added, to further perfecting the drug formulation of the Chinese herbal oral paste of the present invention.

For another example, in the process of the processing method for the Chinese herbal oral paste of the present invention, in the concentration step, when the drug juice is concentrated to the vegetarian paste, a wild jujube shell powder is added evenly with stirring. The wild jujube shell powder above is obtained by sufficiently smashing and grinding the wild jujube shell, with a particle size of 100-400 micrometers. The wild jujube shell powder has the main components of cellulose and lignin, has quite advanced pores in the powder particles, and is a natural drug carrier. When added to the Chinese herbal oral paste, the pores inside the wild jujube shell powder will be filled up with the drug components of the Chinese herbal oral paste. Since the cellulose and lignin cannot be digested or absorbed in vivo, they can serve an effect of sustained release, and a small part of the drug components stored in the wild jujube shell powder can be released continuously, so that the drug is present in the digestive system for an extended period of time. The phenomenon that the drug components are wasted as the digestive system cannot absorb a large amount of drug components within a short period of time will not occur. The wild jujube shell powder is added in an amount of 1%-3% of the gelatin type drugs, and should not be used in an excessive amount, because the excessive amount, on one hand, will deteriorate the form quality of the oral paste, and on the other hand, will increase the burdens of the intestines and stomach as it cannot be absorbed by the human body.

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A Chinese herbal oral paste for conditioning yang deficiency constitution, comprising the following raw material components in parts by weight: 4-20 parts of prepared rehmannia root, 10-20 parts of Chinese yam, 10-20 parts of dogberry, 5-15 parts of seed of Chinese dodder, 5-15 parts of angelica, 5-15 parts of eucommia ulmoides, 9-21 parts of lycium barbarum, 3-9 parts of cinnamon, 8-22 parts of fuling, 3-9 parts of cortex moutan, 3-9 parts of rhizoma alismatis, 6-18 parts of white atractylodes rhizome, 10-30 parts of radix polygonum multiflorum preparata, 4-8 parts of dried ginseng, 5-15 parts of processed aconite root, 4-8 parts of prepared liquorice root, 3-9 parts of cumin, 7-17 parts of herba cistanche, 3-9 parts of fruit of Chinese magnoliavine, 5-15 parts of radix cyathulae, 5-15 parts of raspberry, 1-5 parts of nutmeg, 5-15 parts of fructus broussonetiae, 7-23 parts of epimedium, 5-15 parts of fructus psoraleae, 8-22 parts of rhizoma curculiginis, 3-9 parts of rhizoma acori graminei, 7-17 parts of morinda officinalis, 1-5 parts of human placenta, 7-23 parts of cynomorium songaricum, 7-23 parts of bitter cardamon, 5-15 parts of semen allii tuberosi, 10-30 parts of antler gelatin, 15-35 parts of xylitol, 20-40 parts of walnut kernel, and 20-40 parts of donkey-hide gelatin.

2. The Chinese herbal oral paste for conditioning yang deficiency constitution of claim 1, comprising the following raw material components in parts by weight: the prepared rehmannia root is 8-16 parts by weight, the Chinese yam is 12-18 parts by weight, the dogberry is 12-18 parts by weight, the seed of Chinese dodder is 8-12 parts by weight, the angelica is 8-12 parts by weight, the eucommia ulmoides is 8-12 parts by weight, the lycium barbarum is 12-18 parts by weight, the cinnamon is 5-7 parts by weight, the fuling is 12-18 parts by weight, the cortex moutan is 5-7 parts by weight, the rhizoma alismatis is 5-7 parts by weight, the white atractylodes rhizome is 9-15 parts by weight, the radix polygonum multiflorum preparata is 15-25 parts by weight, the dried ginseng is 5-7 parts by weight, the processed aconite root is 8-12 parts by weight, the prepared liquorice root is 5-7 parts by weight, the cumin is 5-7 parts by weight, the herba cistanche is 10-14 parts by weight, the fruit of Chinese magnoliavine is 5-7 parts by weight, the radix cyathulae is 8-12 parts by weight, the raspberry is 8-12 parts by weight, the nutmeg is 2-4 parts by weight, the fructus broussonetiae is 8-12 parts by weight, the epimedium is 11-19 parts by weight, the fructus psoraleae is 8-12 parts by weight, the rhizome curculiginis is 11-19 parts by weight, the rhizoma acori graminei is 5-7 parts by weight, the morinda officinalis is 10-14 parts by weight, the human placenta is 2-4 parts by weight, the cynomorium songaricum is 11-19 parts by weight, the bitter cardamon is 11-19 parts by weight, the semen allii tuberosi is 8-12 parts by weight, the antler gelatin is 16-24 parts by weight, the xylitol is 20-30 parts by weight, the walnut kernel is 25-35 parts by weight, and the donkey-hide gelatin is 25-35 parts by weight.

3. The Chinese herbal oral paste for conditioning yang deficiency constitution of claim 1, comprising the following raw material components in parts by weight: the prepared rehmannia root is 12 parts by weight, the Chinese yam is 15 parts by weight, the dogberry is 15 parts by weight, the seed of Chinese dodder is 10 parts by weight, the angelica is 10 parts by weight, the eucommia ulmoides is 10 parts by weight, the lycium barbarum is 15 parts by weight, the cinnamon is 6 parts by weight, the fuling is 15 parts by weight, the cortex moutan is 6 parts by weight, the rhizoma alismatis is 6 parts by weight, the white atractylodes rhizome is 12 parts by weight, the radix polygonum multiflorum preparata is 20 parts by weight, the dried ginseng is 6 parts by weight, the processed aconite root is 10 parts by weight, the prepared liquorice root is 6 parts by weight, the cumin is 6 parts by weight, the herba cistanche is 12 parts by weight, the fruit of Chinese magnoliavine is 6 parts by weight, the radix cyathulae is 10 parts by weight, the raspberry is 10 parts by weight, the nutmeg is 3 parts by weight, the fructus broussonetiae is 10 parts by weight, the epimedium is 15 parts by weight, the fructus psoraleae is 10 parts by weight, the rhizoma curculiginis is 15 parts by weight, the rhizoma acori graminei is 6 parts by weight, the morinda officinalis is 12 parts by weight, the human placenta is 3 parts by weight, the cynomorium songaricum is 15 parts by weight, the bitter cardamon is 15 parts by weight, the semen allii tuberosi is 10 parts by weight, the antler gelatin is 20 parts by weight, the xylitol is 25 parts by weight, the walnut kernel is 30 parts by weight, and the donkey-hide gelatin is 30 parts by weight.

4. A processing method for the Chinese herbal oral paste for conditioning yang deficiency constitution of claim 1, comprising the following steps in sequence: preparation of materials, soaking, decoction, concentration, and collecting an oral paste.

5. The processing method for the Chinese herbal oral paste for conditioning yang deficiency constitution of claim 4, wherein the step of preparation of materials is: measuring raw materials of formula amounts according to composition of the Chinese herbal oral paste, and cleaning raw materials, except antler gelatin, donkey-hide gelatin, and xylitol, for subsequent use.

6. The processing method for the Chinese herbal oral paste for conditioning yang deficiency constitution of claim 5, wherein the soaking step is: soaking the cleaned raw materials with 8-10 folds of water for 8-15 h, with the water over the raw materials by 10-20 cm.

7. The processing method for the Chinese herbal oral paste for conditioning yang deficiency constitution of claim 6, wherein the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

8. The processing method for the Chinese herbal oral paste for conditioning yang deficiency constitution of claim 7, wherein the concentration step is: boiling and skimming the supernatant liquid resulted in the decoction step, followed by decoction concentration and stirring with gentle heat, until a drug liquid does not disperse when being dropped on paper, to obtain a vegetarian paste.

9. The processing method for the Chinese herbal oral paste for conditioning yang deficiency constitution of claim 8, wherein the step of collecting an oral paste is: pouring xylitol, and melted antler gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

10. The processing method for the Chinese herbal oral paste for conditioning yang deficiency constitution of claim 9, wherein the melting step is: smashing lumps of antler gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

11. A processing method for the Chinese herbal oral paste for conditioning yang deficiency constitution of claim 2, comprising the following steps in sequence: preparation of materials, soaking, decoction, concentration, and collecting an oral paste.

12. The processing method for the Chinese herbal oral paste for conditioning yang deficiency constitution of claim 11, wherein the step of preparation of materials is: measuring raw materials of formula amounts according to composition of the Chinese herbal oral paste, and cleaning raw materials, except antler gelatin, donkey-hide gelatin, and xylitol, for subsequent use.

13. The processing method for the Chinese herbal oral paste for conditioning yang deficiency constitution of claim 12, wherein the soaking step is: soaking the cleaned raw materials with 8-10 folds of water for 8-15 h, with the water over the raw materials by 10-20 cm.

14. The processing method for the Chinese herbal oral paste for conditioning yang deficiency constitution of claim 13, wherein the decoction step is: decocting the soaked drug materials over flame, firstly boiling the drug materials with high heat to sufficiently expand, then boiling the drug materials with low heat for 1-2 hours of decoction, then filtering the drug juice with gauze, then soaking filtered dregs of decoction with clear water and decocting the soaked dregs of decoction with low heat for 1 hour, repeated 2-4 times, combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

15. The processing method for the Chinese herbal oral paste for conditioning yang deficiency constitution of claim 14, wherein the concentration step is: boiling and skimming the supernatant liquid resulted in the decoction step, followed by decoction concentration and stirring with gentle heat, until a drug liquid does not disperse when being dropped on paper, to obtain a vegetarian paste.

16. The processing method for the Chinese herbal oral paste for conditioning yang deficiency constitution of claim 15, wherein the step of collecting an oral paste is: pouring xylitol, and melted antler gelatin and donkey-hide gelatin into the vegetarian paste respectively, cooking them slowly with low heat, stirring them continuously with a shovel, until the juice coagulates into beads when being dropped into clear water and does not disperse, and canning the resulted oral paste.

17. The processing method for the Chinese herbal oral paste for conditioning yang deficiency constitution of claim 16, wherein the melting step is: smashing lumps of antler gelatin and donkey-hide gelatin into small gelatin pieces or gelatin powder, soaking and softening the small gelatin pieces or the gelatin powder in Shaoxing wine, heating the softened small gelatin pieces or gelatin powder with water in a steamer until they are completely melted.

18. A processing method for the Chinese herbal oral paste for conditioning yang deficiency constitution of claim 3, comprising the following steps in sequence: preparation of materials, soaking, decoction, concentration, and collecting an oral paste.

19. The processing method for the Chinese herbal oral paste for conditioning yang deficiency constitution of claim 18, wherein the step of preparation of materials is: measuring raw materials of formula amounts according to composition of the Chinese herbal oral paste, and cleaning raw materials, except antler gelatin, donkey-hide gelatin, and xylitol, for subsequent use.

20. The processing method for the Chinese herbal oral paste for conditioning yang deficiency constitution of claim 19, wherein the soaking step is: soaking the cleaned raw materials with 8-10 folds of water for 8-15 h, with the water over the raw materials by 10-20 cm.

\* \* \* \* \*